(12) United States Patent
Berlin

(10) Patent No.: US 7,008,770 B1
(45) Date of Patent: Mar. 7, 2006

(54) METHOD FOR THE CONTROLLED IMPLEMENTATION OF COMPLEX PCR AMPLIFICATIONS

(75) Inventor: Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 393 days.

(21) Appl. No.: 10/130,094

(22) PCT Filed: Nov. 12, 2000

(86) PCT No.: PCT/DE00/03973

§ 371 (c)(1),
(2), (4) Date: May 13, 2002

(87) PCT Pub. No.: WO01/36669

PCT Pub. Date: May 25, 2001

(30) Foreign Application Priority Data

Nov. 12, 1999 (DE) .............................. 199 56 203
Oct. 12, 2000 (DE) .............................. 100 51 714

(51) Int. Cl.
  *C12Q 1/68* (2006.01)
  *C07H 21/04* (2006.01)

(52) U.S. Cl. ..................... 435/6; 435/91.2; 536/24.3; 536/25.32

(58) Field of Classification Search ................ 435/6, 435/91.2; 536/24.3, 25.32
See application file for complete search history.

(56) References Cited

U.S. PATENT DOCUMENTS 5,840,549 A * 11/1998 First et al. ................ 435/91.2
6,083,701 A * 7/2000 Reeve .......................... 435/6
6,653,070 B1 11/2003 Olek

FOREIGN PATENT DOCUMENTS

DE        19801661 A1    7/1999

OTHER PUBLICATIONS

Wang et al. Science, 1998, vol. 280, p. 1077-1082.*

* cited by examiner

*Primary Examiner*—Kenneth R. Horlick
*Assistant Examiner*—Joyce Tung
(74) *Attorney, Agent, or Firm*—Kriegsman & Kriegsman

(57) ABSTRACT

A method is described for controllably conducting complex PCR amplifications, wherein at least the following steps are conducted:

a) PCR amplification with at least 50 primers of a first type (type 1) of different sequence, which are complementary to one of the strands of a random DNA sample, and also with a primer or a library of primers of a second type (type 2), which is complementary to the other strand of the DNA sample used, wherein the type 2 primers contain a first label (label 1);

b) hybridizing of the amplified products to an oligomer array, which comprises oligonucleotides that hybridize to the primers utilized in the PCR reaction or to oligonucleotides that are complementary to these;

or hybridizing of the amplified products to an oligomer array, which contains oligomers complementary to the primers utilized in the PCR reaction;

c) length determination of the amplified products bound to the array by a second label (label 2) which can be correlated with the length of the respective DNA fragment, and which is different from the first label (label 1) in step a) and d) quantification of the signals originating from label 1 and label 2 at each site of the oligonucleotide array relevant for the analysis.

14 Claims, No Drawings

METHOD FOR THE CONTROLLED IMPLEMENTATION OF COMPLEX PCR AMPLIFICATIONS

The invention concerns a method for the controllable conducting of complex PCR amplifications.

Complex PCR amplifications, e.g., "whole genome amplifications", are utilized for the simultaneous propagation of a multiple number of fragments of DNA samples. The highly diverse fragments that are obtained may be utilized for such purposes as genotyping, mutation analysis and related subject areas.

These methods, of course, can only be validated and calibrated with difficulty, based on their complexity and the fact that a large portion of the amplified sequence is for the most part unknown. The present invention is concerned with complex PCR amplifications, which are accessible to complete analysis by means of a fitted oligomer array.

PCR reactions (polymerase chain reactions) are normally conducted with two specifically binding primers, wherein one is complementary to the (+) strand, while the other is complementary to the (−) strand of the template to be amplified. The objective of such an amplification is to make many copies of a specific fragment of the template DNA, which is usually precisely defined and whose base sequence is known for the most part or is completely known.

PCR reactions are also known, which utilize more than two different primers. These primarily serve for the simultaneous amplification in one vessel of several fragments, whose base sequence is known at least for the most part. In this case also, the utilized primers specifically bind to defined segments of the template DNA. In such cases, one speaks of "multiplex PCR", which has for the most part the objective only to be able to amplify several fragments simultaneously and thus to save material and experimental expenditure.

PCR reactions, which amplify fragments that are not previously known, may be conducted with primers that do not bind specifically to defined regions. These primers are designed so that complementary binding sites in the template DNA, when considered statistically, should occur several times. In this case we speak of complex PCR amplifications. Such amplifications may be utilized in order to amplify in a statistically distributed manner, a specific fraction, for example, of a genome. The complexity of the amplified products can be regulated each time, depending on the number of possible binding sites of a primer in the genome. The primer may either be very short, make available universally pairing bases, or however, may be synthesized as a combinatory library of sequences. "Whole genome amplifications" are described, for example, in the following publications: L. P. Zhang, et al.; Whole genome amplification from a single cell: Implications for genetic analysis; Proc. Natl. Acad. Sci. USA (1992), 89, 5847–51; K. Kristjansson, et al.; Preimplantation single cell analyses of dytrophin gene deletion using whole genome amplification; Nature Genetics (1994), 6, 19–23; P. O. Brown; Genome scanning methods, Current Opinion in Genetics and Development (1994), 4, 366–73; M. T. Barrett, et al.; Genotypic analysis of multiple loci in somatic cells by whole genome amplification; Nucl. Acids Res. (995), 23, 3488–92; D. Grothues, et al. PCR amplification of megabase DNA with tagged random primers (T-PCR); Nucl. Acids Res. (1993), 21, 1321–2; J. Welsh et al.; Fingerprinting genomes using PCR with arbitrary primers; Nucl. Acids Res. (1990), 18, 7213–8; V. G. Cheung et al.; Whole genome amplification using a degenerate oligonucleotide primer allows hundreds of genotypes to be performed on less than one nanogram of genomic DNA; Proc. Natl. Acad. Sci. USA (1996), 93, 14676–9.

In the field of DNA chips, one principle that has advanced the furthest in all developments is that described, for example, in U.S. Pat. No. 5,593,839, U.S. Pat. No. 5,999,695 or U.S. Pat. No. 5,631,734. However, a number of other DNA chips with different properties for special applications are also known (e.g., U.S. Pat. No. 5,667,667, U.S. Pat. No. 5,525,464 or U.S. Pat. No. 5,492,806 or e.g., Goffeau, A., Nature 385, 202–203; Weiler, J. and Hoheisel, J., Anal. Biochem. 243, 218–227; Chee, M. et al., Science 274, 610–614). More recent publications report on a commercially available HIV chip, which permits the investigation of the complete HIV genome. Fluorescently labeled PCR products of the sample to be investigated are hybridized to up to 400,000 oligonucleotides. The signals are evaluated by means of CCD cameras or special fluorescence scanners. The capacity of such systems for allele-specific hybridization, which has been known for a long time, is utilized. This means: A signal remains at the end of the hybridizing and washing procedures only in those places where the sample is absolutely complementary to a fixed oligonucleotide. A known gene sequence can be investigated for mutations, since not only is each partial region of the entire sequence found in the form of oligonucleotide sequences on the matrix, but since this also applies to any possible deviation from the normal sequence. The efficiency of the chip procedure is partly due to the fact that the sequence information of a multiple number of genes or gene sites is obtained with two simple working steps, namely hybridizing and washing.

The detection of different labeled nucleotide analogs incorporated in one amplification or DNA labeled at the 5' end on one (no matter how it is constituted) DNA chip can be conducted in many different ways. One possibility is detection with a CCD camera, which records fluorescence signals, which indicate that a fluorescently labeled random sequence has been bound on the chip.

5-Methylcytosine is the most frequent covalently modified base in the DNA of eukaryotic cells. For example, it plays a role in the regulation of transcription, genomic imprinting and in tumorigenesis. The identification of 5-methylcytocytosine as a component of genetic information is thus of considerable interest. 5-Methylcytosine positions, however, cannot be identified by sequencing, since 5-methylcytosine has the same base-pairing behavior as cytosine. In addition, in the case of a PCR amplification, the epigenetic information, which is borne by 5-methylcytosines, is completely lost.

Several methods are known, which solve this problem. For the most part, a chemical reaction or enzymatic treatment of the genomic DNA is conducted, as a consequence of which cytosine bases can be distinguished from methylcytosine bases. A current method is the reaction of genomic DNA with bisulfite, which leads to a conversion of cytosine bases to uracil in two steps after alkaline hydrolysis (Shapiro, R., Cohen, B., Servis, R. Nature 227, 1047 (1970)). 5-Methylcytosine under these conditions remains unchanged. The conversion of C to U leads to a modification of the base sequence, from which the original 5-methylcytosines can now be determined by sequencing (only these will still supply a band in the C lane).

Matrix-assisted Laser Desorption/Ionization Mass Spectrometry (MALDI) is a new, very high-performing development for the analysis of biomolecules (Karas, M. and Hillenkamp, F. 1988. Laser desorption ionization of proteins with molecular masses exceeding 10,000 daltons. Anal.

Chem. 60: 2299–2301). An analyte molecule is embedded in a matrix absorbing in the UV. The matrix is evaporated in vacuum by a short laser pulse and the analyte is transported unfragmented into the gas phase. An applied voltage accelerates the ions in a field-free flight tube. Ions are accelerated to very different degrees based on their different masses. Smaller ions reach the detector sooner than larger ones. The time of flight is converted into the mass of the ions.

Technical innovations in hardware have significantly improved the method. Delayed extraction (DE) should be mentioned. For DE, the acceleration voltage is turned on with a delay relative to the laser pulse and in this way an improved resolution of the signals is achieved, since the number of collisions is reduced.

Multiple fluorescently labeled probes are used for the scanning of an immobilized DNA array. Particularly suitable for fluorescence labeling is the simple introduction of Cy3 and Cy5 dyes to the 5' OH of the respective probe. The fluorescence of the hybridized probes is detected, for example, by means of a confocal microscope. Along with many others, the dyes Cy3 and Cy5 are commercially available. Nucleotides, which, for example, bear a Cy5 label and which can be incorporated in a PCR reaction are also commercially available (Amersham Pharmacia).

Complex amplifications, which are described in the prior art, in any case, can be controlled statistically overall in their result. However, it is practically impossible to determine the number and length of the different fragments produced after an amplification conducted with two nonspecifically binding primers.

The object of the present invention is thus to overcome the disadvantages of the methods known in the prior art.

The object is solved by a method for the controllable conducting of complex PCR amplifications, wherein at least the following steps are carried out:

a) PCR amplification with at least 50 primers of a first type (type 1) of different sequence, which are complementary to one of the strands of a random DNA sample, and which also contains a primer or a library of primers of a second type (type 2), which is complementary to the other strand of the DNA sample used, wherein the type-2 primers contain a first label (label 1).

b) hybridizing of the amplified products to an oligomer array, which comprises oligonucleotides that hybridize to the primers utilized in the PCR reaction or to nucleotides complementary to these;

or hybridizing of the amplified products to an oligomer array, which contains oligomers complementary to the primers utilized in the PCR reaction;

c) length determination of the amplified products bound to the array by means of a second label (label 2) which can be correlated with the length of the respective DNA fragment, and which is different from the first label (label 1) in step a) and d) quantification of the signals originating from label 1 and label 2 at each site of the oligonucleotide array relevant for the analysis.

In this connection, hybridizing is understood as an assembly of two DNA strands in the sense of Watson-Crick base pairing, wherein no more than 25% of base pairs that do not correspond to the Watson-Crick rules occur over a random segment of 8 bases in the double strand that is formed.

It is advantageously preferred according to the invention that a PCR amplification is conducted with at least 50 type-1 primers of different sequence, which are complementary to the (+) strand of a random DNA sample, and with a type-2 primer or a library of type-2 primers, which is complementary to the (−) strand, wherein the type-2 primers contain a label 1.

It is equally preferred according to the invention that a PCR amplification is conducted with at least 50 type-1 primers of different sequence, which are complementary to the (−) strand, and with a type-2 primer or a library of type-2 primers, which is complementary to the (+) strand, wherein the type-2 primers contain a label 1.

It is particularly preferred that one selects at least 50 type-1 primers [to be] used and that these primers hybridize specifically to the DNA to be amplified, whereas one selects type-2 primers complementary to the counterstrand such that the latter does not specifically hybridize.

It is preferred according to the invention that the primer of the counterstrand comprises less than 15 bases. It is most particularly preferred that the primer of the counterstrand comprises less than 12 bases.

It is also preferred according to the invention that the primer of the counterstrand comprises positions with universal bases or degenerated positions.

It is also preferred according to the invention that the primer of the counterstrand is produced by combinatory synthesis.

It is preferred in the method according to the invention that label 1 and label 2 are fluorescent labels.

It is particularly preferred that label 1 and label 2 are fluorescent labels and/or removable mass labels that can be detected in a mass spectrometer.

It is particularly preferred that the ratio between the signals proceeding from label 1 and label 2 is determined at any site of the array relevant for the analysis.

It is also preferred according to the invention that the type-1 primers that are used only contain the bases T, A and C, or the bases T, A, and G.

It is also preferred according to the invention that the DNA of the amplification be chemically treated in such a way that 5-methylcytosine and cytosine react differently and a change in base-pairing behavior results for one of these bases by means of the treatment.

It is most preferably preferred that the treatment of the DNA prior to the amplification be conducted by means of a bisulfite solution (=disulfite, hydrogen sulfite).

In this invention, a complex amplification is thus described, which is of such a type that the disadvantages of the prior art are overcome.

The subject of the present invention is a method for the controllable conducting of complex PCR amplifications. For this purpose, a PCR amplification is first conducted with at least 50 type-1 primers and a type-2 primer of primer library, whereby the at-least 50 type-1 primers are all different with respect to their sequence and all are also complementary to the (+) strand of a random DNA sample investigated with the use of this method. Also, the type [2] primers or the library of type-2 primers are complementary to the (−) of the DNA sample investigated with the use of this method. Alternatively, type-1 primers are complementary to the (−) strand and type-2 primers are complementary to the (+) strand. The type-2 primers contain a type-1 label.

In a particularly preferred variant of the method, the at-least 50 type-1 primers utilized hybridize specifically to the DNA to be amplified, while the type 2 primer complementary to the counterstrand does not hybridize specifically, i.e., it can bind several sites of the DNA sample to be investigated under the selected reaction conditions. In a particularly preferred variant of the method, the type-2 primer contains fewer than 15 bases. In a preferred variant of the method, the type-2 primer contains fewer than 12 bases.

The type-2 primer can also preferably contain degenerated base positions, i.e., positions which can bind in a comparable manner to different bases of the counterstrand, e.g., to A, G or T. So-called universal bases may also be used, which can bind to complementary T, C, G and A nucleobases. In a particularly preferred variant of the method, the type-2 primer is produced by combinatory synthesis, so that a library of primers of equal length is obtained. Consequently, primer libraries are used, which contain different bases at specific positions in a given sequence.

In a preferred variant of the method, label 1 of the type-2 primer is a fluorescent label. In another particularly preferred variant of the method, the label of the type-2 primer is a mass label, which can be used for the detection of this primer in a mass spectrometer. In a particularly preferred embodiment, detection is conducted in a MALDI mass spectrometer, whereby the mass label is removed either by exposure to the laser of the mass spectrometer or by contact with the MALDI matrix.

In another, particularly preferred variant of the method, the type-1 primers used either contain only the bases T, A and C or the bases T, A and G.

In the second step, the amplified products are hybridized to an oligomer array, which comprises oligonucleotides that hybridize to the primers utilized in the PCR reaction or to oligonucleotides complementary to these. The oligomers of the array are preferably oligonucleotides or PNA oligomers. Normally, they hybridize only to one strand of an amplified product, preferably to the strand that contains label 1 and accordingly comprises one of the type-2 primers.

Alternatively, in the second step of the method, the amplified products are hybridized to an oligomer array, which contains oligomers complementary to the primers utilized in the PCR reaction.

In the third step of the method, a length determination is now conducted of the amplified products bound to each site of the array relevant for the analysis by means of a label 2, which is different from label 1 of the first step of the method and can be correlated with the length of the respective DNA fragment. In a preferred variant of the method, label 2 is a fluorescent label. In another particularly preferred variant of the method, the label of the type-2 primer is a mass label, which can be used for the detection of this primer in a mass spectrometer. In a particularly preferred embodiment, detection is undertaken in a MALDI mass spectrometer, wherein the mass label is removed either by exposure to the laser of the mass spectrometer or by contact with the MALDI matrix. Depending on the length of the respective amplified product, label 2 is either bound to this product or is integrated in it in the amplification. This can result preferably with the use of triphosphates with fluorescent or mass labels in the amplification. In another, particularly preferred variant of the method, the length is determined by hybridizing nonspecifically binding oligonucleotides or peptide nucleic acids, which again bear a fluorescent label and/or a mass label. The fluorescent labels and mass labels must be different from those of the type-2 primer.

In the fourth step of the method according to the invention, the signals originating from label 1 and label 2 at each site of the oligonucleotide array that is relevant for the analysis are quantified. In a particularly preferred variant of the method, the ratio of the intensities of the signals proceeding from label 1 and label 2 is determined at any site of the array relevant for the analysis. In a preferred variant of the method, it is determined which type-1 primers actually have contributed to an amplification and also it is determined what the average length is of the amplified product that proceeds from one of the primers.

In a particularly preferred variant of the method, the DNA sample is chemically treated prior to the amplification in such a way that 5-methylcytosine and cytosine react differently and a change in base-pairing behavior results for one of these bases due to the treatment. In a particularly preferred variant of the method, this is achieved by a treatment of the DNA prior to the amplification with a bisulfite (=disulfite, hydrogen sulfite) solution. With the use of this variant, the method serves for the controllable production of complex DNA amplified products, which are used for the investigation of cytosine methylation patterns in the respective DNA sample.

The following examples explain the invention.

EXAMPLE 1

Complex Amplification with 50 Forward Primers and One Reverse Primer and Their Controls The object of conducting controlled complex amplifications is assured by two components of the method:

1. First of all, the amplification is conducted in such a way that there are two types of primers. In the simplest case of the method described in the principal claim, 50 primers of different sequence are used, which bind to one of the strands of the template, as well as one primer, which binds to the corresponding counterstrand. Accordingly, amplified products will be produced, in which one of the components of the double-stranded product will always be one of the 50 type-1 primers and also the type-2 primer. In order to make this possible, the type-2 primer must hybridize to the template statistically substantially more frequently than the type-1 primers. For example, type-1 primers bind specifically, but the type-2 primers do not, and these latter primers may either be very short, or however, preferably can contain so-called wobble positions (i.e. positions at which different bases can be found) or degenerated bases, wherein the latter are bases that do not occur naturally in DNA, which can enter into nonspecific base pairings with A, C, T and G or a large aliquot of these bases.

This type of amplification is particularly advantageous in the case when the base composition of the (+) and (−) strands of the double-stranded template are essentially different, since only then is it assured that type-2 primers can hybridize only to one strand and accordingly only with type-1 primers and cannot form amplified products with other type-2 primers that hybridize much more frequently.

This difference in base composition is the case, for example, when genomic DNA has been treated with sodium bisulfite. In this case, the treated strand consists almost exclusively of the bases A, T and G, but the complementary strand consists almost exclusively of A, T and C. This can be considered a great advantage in designing primer sequences.

2. The method conducted in this way has the advantage that after the amplification, a control can now be made of whether the complex PCR has produced one product for each of the primers used. For this purpose, the amplified products are hybridized to an oligomer array, which contains probes that are complementary to type-1 primers (at least 50 different ones), or, in a particularly preferred manner, sequence-homologous probes. In the simplest case, the 50 primers utilized are immobilized on a surface and the complex amplified products are hybridized thereto. However, since only the type-2 primers bear a label, only the positions with a label on which these primers are found that have also produced a product in the amplification are provided on the surface due to hybridizing. Thus, it can be easily identified which parts of the complex amplification were successful and also a quality control can be easily conducted.

In order to also be able to determine the correct length of each of the synthesized amplified products, another label can be incorporated in the amplification. In the simplest case, this is the length of the product itself in the form of molecular weight, which can then be detected, for example, by mass spectrometry. However, preferably, the label would be introduced during the PCR by incorporation of labeled nucleotides, for example, by a Cy3-labeled dCTP. Since it is known how many cytosine bases are found in the amplified product and it is also known how many labeled dCTPs are incorporated in comparison to unlabeled dCTPs that are also present, the length of the amplified product can be calculated, or at least the reproducibility of the amplification can be detected in this way. A normalizing is necessary for the calculation, which takes into consideration the different quantities of amplified product that are bound, but this can be done very easily, since the measurable number of labels 1 on the type 2 primer is linearly correlated with the bound amplified product.

EXAMPLE 2

Conducting a Complex PCR

Genomic DNA is converted to bisulfite-treated DNA (Olek et al., Nucl. Acids Res. 1996, 24, 5064–5066; prior art). In this example, the complex amplification is conducted with 64 type-1 primer oligonucleotides and 4 type-2 primer oligonucleotides. The type-2 primer oligonucleotides are labeled with the fluorescent dye Cy5. The following primer sequences are used (only the specific part is listed; for equilibrating the annealing temperature, it is filled with nonspecifically binding positions ("wobbles")):

Type 1:
TAGTTAGTGTTTAGG SEQ ID NO: 1
ATTTATTTATTTTTT SEQ ID NO: 2
ATTTAGATTTTATTG SEQ ID NO: 3
GTTTTTGTATTTAAG SEQ ID NO: 4
AGTAGAGTTGAGAAG SEQ ID NO: 5
GTTTAGATAGGGTA SEQ ID NO: 6
TTTATTATGATTTTG SEQ ID NO: 7
GTATTATTGTGTTTG SEQ ID NO: 8
TGGTTAATAGTAATG SEQ ID NO: 9
TAGTAATTGTATTGG SEQ ID NO: 10
TTTAGTATTTTGTTG SEQ ID NO: 11
TAAGTTTTATGAGGT SEQ ID NO: 12
GATTTGTTTTAGGTA SEQ ID NO: 13
TGATTAATATGGTGA SEQ ID NO: 14
GAATAGAAATTAGGG SEQ ID NO: 15
TATAAGGTTAGGAGA SEQ ID NO: 16
TTAGAGGTTTTTGAG SEQ ID NO: 17
ATTTTTGTTTGTAGA SEQ ID NO: 18
GTTGGATAGAAGAGT SEQ ID NO: 19
TAAAAAATTAGTTGG SEQ ID NO: 20
GTATGGTGGTTAGAT SEQ ID NO: 21
TAATGTAGGTTAGGA SEQ ID NO: 22
AAGTGGTTAGGTATG SEQ ID NO: 23
GAATTGAGGTAATGT SEQ ID NO: 24
TAATTTGAGGTTAGG SEQ ID NO: 25
TAAAGGAAAGTAGGT SEQ ID NO: 26
TTTGGAAAAATATAG SEQ ID NO: 27
AATTAATATGGAAAG SEQ ID NO: 28
GAGTAATGGAAAGAG SEQ ID NO: 29
TATTTAAGAGGTTGA SEQ ID NO: 30
GAGTTGGGTATTAGT SEQ ID NO: 31
TTTAGAGAGGTGAAG SEQ ID NO: 32
GTTTTAGATTTGTTG SEQ ID NO: 33
GTTTTATGAGAGGTT SEQ ID NO: 34
TTGTATTTGGATAGA SEQ ID NO: 35
GAAAGTTGTTGTTGT SEQ ID NO: 36
TGAATTTGTTTTTG SEQ ID NO: 37
GGTTAGTAGGGTTAT SEQ ID NO: 38
GTTTTAGGTAGAGGA SEQ ID NO: 39
TTAGGGAAGTATTAT SEQ ID NO: 40
GTTTGGTGGTTA SEQ ID NO: 41
GAGAGGTTATATTTG SEQ ID NO: 42
GGTTAGTTAGGTTAT SEQ ID NO: 43
AGTAAATATTGAAAG SEQ ID NO: 44
TTGAGTTTTTTATAG SEQ ID NO: 45
TTGAATTTTTATTTA SEQ ID NO: 46
TGATATTAATTTGTT SEQ ID NO: 47
TTTGGTTATTAGAGT SEQ ID NO: 48
ATTTAGTTTATTTGT SEQ ID NO: 49
TAGGTTATTTTTGTA SEQ ID NO: 50
TATAGAGTATTGGTG SEQ ID NO: 51
TTAGATTTTAATAGG SEQ ID NO: 52
GGTTAGTTATGTATT SEQ ID NO: 53
TAGTAGGTTGTTTAG SEQ ID NO: 54
AATTTTAGGTTGTT SEQ ID NO: 55
GTGAGGATATTTATT SEQ ID NO: 56
GTTATAAGTTAAGGA SEQ ID NO: 57
TTTATTATAGAGGAG SEQ ID NO: 58
TTGTGGTTTGGA SEQ ID NO: 59
TGATTTTAGATGTAG SEQ ID NO: 60
GAGGTTAAAAGGT SEQ ID NO: 61
TTAAGGTATATTAGG SEQ ID NO: 62
TTTGAAGTAATTGTA SEQ ID NO: 63
GTTGTATTGGATAGT SEQ ID NO: 64

Type 2:
ACACTCCAACCT SEQ ID NO: 65
ACCTCAACCTCC SEQ ID NO: 66
AAAACAAAACCC SEQ ID NO: 67
AAAACAAAACCA SEQ ID NO: 68

The PCR is conducted with the following reaction batch:
Reaction batch complex PCR PCR (25 µl)
1 µl of DNA treated with hydrogen sulfite
2.5 µl of PCR buffer (10×, Qiagen)
1 µl of the mixture of type-[1] primers (64 primer oligonucleotides, 0.78 pmol/µl of each)
1 µl of the mixture of type-2 primers (4 primer oligonucleotides, labeled with Cy5, 12.48 pmol/µl of each).
0.8 µl of dNTPs (25 mM per dNTP, Gibco-BRL)
3 µl of MgCl$_2$ (15 mM)
15.5 µl of water (for molecular biology, Fluka)
0.2 µl of polymerase (1 unit) (HotstarTaq, Qiagen)
The PCR reaction is conducted in the Master Cycler Gradient (Eppendorf, Hamburg) with the following program:
15 min 95° C.
60 s 95° C.
45 s 35° C. ×39
120 s 65° C.
10 min 65° C.
hold at 4° C.

The PCR amplified products that are produced are analyzed by agarose gel electrophoresis (1.5% agarose in 0.5×TBE buffer, Sambrook et al.). For this purpose 4 µl of the PCR batch are subjected to gel electrophoresis. Under the indicated conditions, 64 DNA fragments with the subsequently given primer pairs are simultaneously amplified successfully.

EXAMPLE 3

Preparation of an Unknown Methylated DNA Sample by Means of Multiplex PCR

The following example relates to the production of an unknown methylated DNA sample, which is compared with the hereunder methylated reference DNA from Example 2. A genomic DNA sample is used, which has been cleaved with the restriction enzyme MssI in this case. The sample is then reacted with hydrogen sulfite (=bisulfite, disulfite). One can proceed according to two different methods. The first method (Olek et al., Nucl. Acids Res. 1996, 24, 5064–5066) is a reaction with hydrogen sulfite and a radical trap, wherein the DNA is embedded in agarose. The desulfonation of the DNA is also produced in agarose. The DNA in this case is utilized without additional purification operations in a preamplification (PEP=primer extension preamplification). Alternatively, the DNA is chemically converted without agarose matrix also with hydrogen sulfite (=bisulfite, disulfite) and a radical trap at elevated temperature. An organic reagent, which supports the denaturation, is added, and the batch is incubated at elevated temperature. All cytosine bases are converted to uracil by the treatment with hydrogen sulfite in both methods, whereas methylcytosines remain the same. For the purification of the DNA treated with bisulfite without agarose matrix, the latter is bound to a reversed-phase C18 solid phase and the chemicals are removed by washing with a suitable buffer solution. Then the DNA is eluted with a polar solvent such as, e.g., acetonitrile and water and concentrated to a smaller volume. The preamplification of The DNA treated with hydrogen sulfite is conducted with very short primer oligonucleotides (5'TTATAATGTTTT SEQ ID NO: 69 and 5'-TAATATACTAAT SEQ ID NO: 70).

Reaction batch (20 µl):
1 µl of bisulfite DNA (0.2–1 ng)
2 µl of reaction buffer (10×, Qiagen)
2 µl of dNTPs (10 mM of each dNTP, Fermentas)
1 µl of primer (TTATAATGTTTT SEQ ID NO: 69), 25 pmol
1 µl of primer (TAATATACTAAT SEQ ID NO: 70), 25 pmol
0.2 µl of polymerase (1 unit) (HotstarTaq, Qiagen)
12.8 µl of water (for molecular biology, Fluka)

The subsequent amplification with primer oligonucleotides labeled with Cy5 is produced with the primer oligonucleotides described in Example 2, whereby the same primer oligonucleotide is labeled [with] Cy5. The amplified products are also subjected to an agarose gel electrophoresis for analysis.

EXAMPLE 4

Comparison of the Unknown Methylated DNA Sample With the Hereunder Methylated Reference DNA The comparison of the unknown methylated DNA sample with the hereunder methylated reference DNA is preferably produced by hybridizing onto an oligonucleotide array. Fluorescing points are visible corresponding to the position on the array. It happens that specific points on the array show a clearly increased or decreased fluorescence relative to other points and to the reference DNA, as long as the amplified products are present in comparable concentration in the individual samples to be investigated. The intensity of the fluorescent dye Cy5 (635 nm) is measured in the individual amplified products. The methods of evaluation of fluorescent measurements are known to the person of average skill in the art.

The invention claimed is:

1. A method for the controllable conducting of complex PCR amplifications, said method comprising the steps of:
   a) performing PCR amplification with at least 50 primers of a first type (type 1) of different sequence, which are complementary to one of the strands of a random DNA sample, and which also contains a primer or a library of primers of a second type (type 2), which is complementary to the other strand of the DNA sample used, whereby the type-2 primers contain a first label (label 1), whereby amplified products are produced;
   b) hybridizing the amplified products to an oligomer array, which comprises oligonucleotides that hybridize to the primers utilized in the PCR reaction or to oligonucleotides that are complementary to the primers utilized in the PCR reaction;
   or hybridizing the amplified products to an oligomer array, which contains oligomers complementary to the primers utilized in the PCR reaction;
   c) determining the length of the amplified products bound to the array by a second label (label 2) which is correlated with the length of the respective DNA fragment, and which is different from the first label (label 1) in step a) and
   d) quantifying the signals originating from label 1 and label 2 at each site of the oligonucleotide array relevant for the analysis.

2. The method according to claim 1, wherein said PCR amplification comprises using at least 50 type-1 primers of different sequence, which are complementary to the (+) strand of a random DNA sample, and also a type-2 primer or a library of type-2 primers, which is complementary to the (−) strand, wherein the type-2 primers contain a label 1.

3. The method according to claim 1, wherein said PCR amplification comprises using at least 50 type-1 primers of different sequence, which are complementary to the (−) strand, and also a type-2 primer or a library of type-2 primers, which is complementary to the (+) strand, wherein the type-2 primers contain a label 1.

4. The method according to claim 1, wherein the at-least 50 type-1 primers used specifically hybridize to the DNA to be amplified, whereas type-2 primers complementary to the counterstrand do not specifically hybridize.

5. The method according to claim 4, wherein the primer of the counterstrand comprises fewer than 15 bases.

6. The method according to claim 4, wherein the primer of the counterstrand comprises fewer than 12 bases.

7. The method according to claim 4, wherein the primer of the counterstrand comprises positions with universal bases or degenerated positions.

8. The method according to claim 4, wherein the primers of the counterstrand are prepared by combinatorial synthesis.

9. The method according to claim 1, wherein label 1 and label 2 are fluorescent labels.

10. The method according to claim 1, wherein label 1 and label 2 are fluorescent labels and/or mass labels that can be removed and can be detected in a mass spectrometer.

11. The method according to claim 9, wherein said quantifying step comprises determining the ratio of the signals proceeding from label 1 and label 2 at each site of the array relevant for the analysis.

12. The method according to claim 1, wherein the type-1 primers used contain either only the bases T, A and C or the bases T, A and G.

13. The method according to claim 1, further comprising, prior to the PCR amplification step, the step of chemically treating the DNA in such a way that 5-methylcytosine and cytosine react differently and a change in base-pairing behavior of one of these bases results due to the treatment.

14. The method according to claim 13, wherein said chemically treating step comprises chemically treating the DNA with a bisulfite solution.

* * * * *

SEQUENCE LISTING

```
<160> NUMBER OF SEQ ID NOS: 70

<210> SEQ ID NO 1
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 1
tagttagtgt ttagg                                                  15

<210> SEQ ID NO 2
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 2
atttatttat ttttt                                                  15
```

```
-continued

<210> SEQ ID NO 3
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 3
atttagattt tattg                                                15

<210> SEQ ID NO 4
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 4
gtttttgtat ttaag                                                15

<210> SEQ ID NO 5
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 5
agtagagttg agaag                                                15

<210> SEQ ID NO 6
<211> LENGTH: 14
<212> TYPE: DNA
<213> ORGANISM: Artificial Sequence
<220> FEATURE:
<223> OTHER INFORMATION: PRIMER TYPE 1

<400> SEQUENCE: 6
tttagagtag ggta                                                 14

<210> SEQ ID NO 7
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 7
tttattatga ttttg                                                15

<210> SEQ ID NO 8
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 8
gtattattgt gtttg                                                15

<210> SEQ ID NO 9
<211> LENGTH: 15
<212> TYPE: DNA
<213> ORGANISM: Artificial Sequence
<220> FEATURE:
<223> OTHER INFORMATION: PRIMER TYPE 1
```

-continued

```
<400> SEQUENCE: 9
tggttaatag taatg                                                15

<210> SEQ ID NO 10
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 10
tagtaattgt attgg                                                15

<210> SEQ ID NO 11
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 11
tttagtattt tgttg                                                15

<210> SEQ ID NO 12
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 12 taagtttat gaggt                                                 15

<210> SEQ ID NO 13
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 13
gatttgtttt aggta                                                15

<210> SEQ ID NO 14
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 14
tgattaatat ggtga                                                15

<210> SEQ ID NO 15
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 15
gaatagaaat taggg                                                15

<210> SEQ ID NO 16
<211> LENGTH: 15
```

```
<212> TYPE: DNA
<213> ORGANISM: Artificial Sequence
<220> FEATURE:
<223> OTHER INFORMATION: PRIMER TYPE 1

<400> SEQUENCE: 16
tataaggtta ggaga                                                    15

<210> SEQ ID NO 17
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 17
ttagaggttt ttgag                                                    15

<210> SEQ ID NO 18
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 18
atttttgttt gtaga                                                    15

<210> SEQ ID NO 19
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 19
gttggataga agagt                                                    15

<210> SEQ ID NO 20
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 20
taaaaaatta gttgg                                                    15

<210> SEQ ID NO 21
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 21
gtatggtggt tagat                                                    15

<210> SEQ ID NO 22
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 22
```

```
taatgtaggt tagga                                                15

<210> SEQ ID NO 23
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 23
aagtggttag gtatg                                                15

<210> SEQ ID NO 24
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 24
gaattgaggt aatgt                                                15

<210> SEQ ID NO 25
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 25
taatttgagg ttagg                                                15

<210> SEQ ID NO 26
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 26
taaaggaaag taggt                                                15

<210> SEQ ID NO 27
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 27
tttggaaaaa tatag                                                15

<210> SEQ ID NO 28
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 28
aattaatatg gaaag                                                15

<210> SEQ ID NO 29
<211> LENGTH: 15
<212> TYPE: DNA
<213> ORGANISM: Artificial Sequence
```

```
<220> FEATURE:
<223> OTHER INFORMATION: PRIMER TYPE 1

<400> SEQUENCE: 29
gagtaatgga aagag                                               15

<210> SEQ ID NO 30
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 30
tatttaagag gttga                                               15

<210> SEQ ID NO 31
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 31
gagttgggta ttagt                                               15

<210> SEQ ID NO 32
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 32
tttagagagg tgaag                                               15

<210> SEQ ID NO 33
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 33
gttttagatt tgttg                                               15

<210> SEQ ID NO 34
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 34
gttttatgag aggtt                                               15

<210> SEQ ID NO 35
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 35
ttgtatttgg ataga                                               15
```

-continued

```
<210> SEQ ID NO 36
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 36
gaaagttgtt gttgt                                                        15

<210> SEQ ID NO 37
<211> LENGTH: 14
<212> TYPE: DNA
<213> ORGANISM: Artificial Sequence
<220> FEATURE:
<223> OTHER INFORMATION: PRIMER TYPE 1

<400> SEQUENCE: 37
tgaatttgtt tttg                                                         14

<210> SEQ ID NO 38
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 38
ggttagtagg gttat                                                        15

<210> SEQ ID NO 39
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 39
gttttaggta gagga                                                        15

<210> SEQ ID NO 40
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 40
ttagggaagt attat                                                        15

<210> SEQ ID NO 41
<211> LENGTH: 12
<212> TYPE: DNA
<213> ORGANISM: Artificial Sequence
<220> FEATURE:
<223> OTHER INFORMATION: PRIMER TYPE 1

<400> SEQUENCE: 41
gtttggtggt ta                                                           12

<210> SEQ ID NO 42
<211> LENGTH: 15
<212> TYPE: DNA
<213> ORGANISM: Artificial Sequence
<220> FEATURE:
<223> OTHER INFORMATION: PRIMER TYPE 1
```

```
<400> SEQUENCE: 42
gagaggttat atttg                                                    15

<210> SEQ ID NO 43
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 43
ggttagttag gttat                                                    15

<210> SEQ ID NO 44
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 44
agtaaatatt gaaag                                                    15

<210> SEQ ID NO 45
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 45
ttgagttttt tatag                                                    15

<210> SEQ ID NO 46
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 46 ttgaatttttt attta                                                   15

<210> SEQ ID NO 47
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 47
tgatattaat ttgtt                                                    15

<210> SEQ ID NO 48
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 48
tttggttatt agagt                                                    15

<210> SEQ ID NO 49
```

```
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 49
atttagttta tttgt                                                    15

<210> SEQ ID NO 50
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 50
taggttattt ttgta                                                    15

<210> SEQ ID NO 51
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 51
tatagagtat tggtg                                                    15

<210> SEQ ID NO 52
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 52
ttagatttta atagg                                                    15

<210> SEQ ID NO 53
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 53
ggttagttat gtatt                                                    15

<210> SEQ ID NO 54
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 54
tagtaggttg tttag                                                    15

<210> SEQ ID NO 55
<211> LENGTH: 14
<212> TYPE: DNA
<213> ORGANISM: Artificial Sequence
<220> FEATURE:
<223> OTHER INFORMATION: PRIMER TYPE 1

<400> SEQUENCE: 55
```

-continued

```
aattttaggt tgtt                                             14

<210> SEQ ID NO 56
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 56
gtgaggatat ttatt                                            15

<210> SEQ ID NO 57
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 57
gttataagtt aagga                                            15

<210> SEQ ID NO 58
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 58
tttattatag aggag                                            15

<210> SEQ ID NO 59
<211> LENGTH: 12
<212> TYPE: DNA
<213> ORGANISM: Artificial Sequence
<220> FEATURE:
<223> OTHER INFORMATION: PRIMER TYPE 1

<400> SEQUENCE: 59
ttgtggtttg ga                                               12

<210> SEQ ID NO 60
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 60
tgattttaga tgtag                                            15

<210> SEQ ID NO 61
<211> LENGTH: 13
<212> TYPE: DNA
<213> ORGANISM: Artificial Sequence
<220> FEATURE:
<223> OTHER INFORMATION: PRIMER TYPE 1

<400> SEQUENCE: 61
gaggttaaaa ggt                                              13

<210> SEQ ID NO 62
<211> LENGTH: 15
<212> TYPE: DNA
```

```
<213> ORGANISM: Artificial Sequence
<220> FEATURE:
<223> OTHER INFORMATION: PRIMER TYPE 1

<400> SEQUENCE: 62
ttaaggtata ttagg                                                15

<210> SEQ ID NO 63
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 63
tttgaagtaa ttgta                                                15

<210> SEQ ID NO 64
<211> LENGTH: 15
<212> TYPE: DNA
<213> ORGANISM: Artificial Sequence
<220> FEATURE:
<223> OTHER INFORMATION: PRIMER TYPE 1

<400> SEQUENCE: 64
gttgtattgg atagt                                                15

<210> SEQ ID NO 65
<211> LENGTH: 12
<212> TYPE: DNA
<213> ORGANISM: Artificial Sequence
<220> FEATURE:
<223> OTHER INFORMATION: PRIMER TYPE 2

<400> SEQUENCE: 65
acactccaac ct                                                   12

<210> SEQ ID NO 66
<211> LENGTH: 12
<212> TYPE: DNA
<213> ORGANISM: Artificial Sequence
<220> FEATURE:
<223> OTHER INFORMATION: PRIMER TYPE 2

<400> SEQUENCE: 66
acctcaacct cc                                                   12

<210> SEQ ID NO 67
<211> LENGTH: 12
<212> TYPE: DNA
<213> ORGANISM: Artificial Sequence
<220> FEATURE:
<223> OTHER INFORMATION: PRIMER TYPE 2

<400> SEQUENCE: 67
aaaacaaaac cc                                                   12

<210> SEQ ID NO 68
<211> LENGTH: 12
<212> TYPE: DNA
<213> ORGANISM: Artificial Sequence
<220> FEATURE:
<223> OTHER INFORMATION: PRIMER TYPE 2

<400> SEQUENCE: 68
aaaacaaaac ca                                                   12
```

```
<210> SEQ ID NO 69
<211> LENGTH: 12
<212> TYPE: DNA
<213> ORGANISM: Artificial Sequence
<220> FEATURE:
<223> OTHER INFORMATION: PREAMPLIFICATION PRIMER

<400> SEQUENCE: 69
ttataatgtt tt                                                              12

<210> SEQ ID NO 70
<211> LENGTH: 12
<212> TYPE: DNA
<213> ORGANISM: Artificial Sequence
<220> FEATURE:
<223> OTHER INFORMATION: PREAMPLIFICATION PRIMER

<400> SEQUENCE: 70
taatatacta at                                                              12
```